(12) United States Patent
Tien et al.

(10) Patent No.: US 10,299,916 B2
(45) Date of Patent: May 28, 2019

(54) BIOPROSTHETIC TISSUE REPAIR AND REINFORCEMENT

(71) Applicant: Medtronic Vascular, Inc., Santa Rosa, CA (US)

(72) Inventors: Tracey Tien, Irvine, CA (US); Carol Eberhardt, Fullerton, CA (US); Kshitija Garde, Fullerton, CA (US); Benjamin Wong, Irvine, CA (US); Wei Wang, Garden Grove, CA (US); Elliot Howard, Redwood City, CA (US); Laura McKinley, Santa Ana, CA (US); Karl Olney, Tustin, CA (US); Taylor Winters, Tustin, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 7 days.

(21) Appl. No.: 15/383,077

(22) Filed: Dec. 19, 2016

(65) Prior Publication Data

US 2017/0196686 A1    Jul. 13, 2017

Related U.S. Application Data

(60) Provisional application No. 62/275,933, filed on Jan. 7, 2016.

(51) Int. Cl.
*A61F 2/24* (2006.01)
*A61L 27/26* (2006.01)
(Continued)

(52) U.S. Cl.
CPC .......... *A61F 2/2415* (2013.01); *A61F 2/2409* (2013.01); *A61F 2/2412* (2013.01);
(Continued)

(58) Field of Classification Search
CPC ........ A61F 2/24; A61F 2/2409; A61F 2/2415; A61F 2/2412; A61L 24/043; A61L 24/06; A61L 27/3625; A61L 27/507; A61L 24/00
See application file for complete search history.

(56) References Cited

U.S. PATENT DOCUMENTS

| 4,378,224 A | 3/1983 | Nimni et al. |
| 4,818,291 A | 4/1989 | Iwatsuki et al. |

(Continued)

FOREIGN PATENT DOCUMENTS

| WO | WO92/12690 | 8/1992 |
| WO | WO96/03159 | 2/1996 |

(Continued)

OTHER PUBLICATIONS

PCT/US2017/012354, The International Search Report and the Written Opinion of the International Searching Authority, dated Jul. 14, 2017, 20pgs.

(Continued)

*Primary Examiner* — Alvin J Stewart

(57) ABSTRACT

A method of reinforcing or repairing a bioprosthetic tissue for use as a prosthetic valve leaflet. The method includes evaluating a bioprosthetic tissue, identifying a defect in the bioprosthetic tissue, and selectively applying an adhesive to a surface of the bioprosthetic tissue at the defect prior to implantation in a patient.

18 Claims, 5 Drawing Sheets

(51) Int. Cl.
*A61L 27/50* (2006.01)
*C09J 4/00* (2006.01)
*C09J 189/00* (2006.01)
*A61L 27/36* (2006.01)
*A61L 24/06* (2006.01)
*A61L 24/10* (2006.01)

(52) U.S. Cl.
CPC ............. *A61L 24/06* (2013.01); *A61L 24/108* (2013.01); *A61L 27/26* (2013.01); *A61L 27/3625* (2013.01); *A61L 27/50* (2013.01); *A61L 27/507* (2013.01); *C09J 4/00* (2013.01); *C09J 189/00* (2013.01); *A61F 2220/005* (2013.01); *A61F 2220/0075* (2013.01); *A61L 2430/20* (2013.01); *A61L 2430/40* (2013.01)

(56) References Cited

U.S. PATENT DOCUMENTS

| | | | | |
|---|---|---|---|---|
| 5,163,955 A * | 11/1992 | Love | ...................... | A61F 2/2412 623/2.15 |
| 5,192,312 A | 3/1993 | Orton | | |
| 5,480,424 A * | 1/1996 | Cox | ...................... | A61F 2/0095 623/2.15 |
| 5,614,587 A * | 3/1997 | Rhee | ...................... | A61K 47/61 525/54.1 |
| 5,713,950 A * | 2/1998 | Cox | ...................... | A61F 2/0095 128/898 |
| 5,744,545 A * | 4/1998 | Rhee | ...................... | A61L 24/102 525/54.1 |
| 6,475,239 B1 * | 11/2002 | Campbell | ............. | A61F 2/2412 264/299 |
| 9,622,863 B2 * | 4/2017 | Karapetian | ............. | A61F 2/246 |
| 2002/0173770 A1 | 11/2002 | Flory et al. | | |
| 2003/0022146 A1 | 1/2003 | Cunanan et al. | | |
| 2004/0059431 A1 | 3/2004 | Plouhar et al. | | |
| 2007/0027528 A1 | 2/2007 | Agnew | | |
| 2007/0050014 A1 * | 3/2007 | Johnson | ................ | A61F 2/2415 623/1.24 |
| 2007/0067021 A1 * | 3/2007 | Haverkost | ............ | A61F 2/2418 623/1.24 |
| 2007/0118210 A1 * | 5/2007 | Pinchuk | ................ | A61F 2/2412 623/1.26 |
| 2007/0154515 A1 * | 7/2007 | Johnson | ................ | A61F 2/0095 424/423 |
| 2009/0117334 A1 * | 5/2009 | Sogard | .................. | A61F 2/2412 428/156 |
| 2009/0181402 A1 * | 7/2009 | Finn | ....................... | B82Y 10/00 435/7.1 |
| 2010/0011564 A1 * | 1/2010 | Millwee | ................ | A61F 2/2415 29/527.3 |
| 2010/0174359 A1 * | 7/2010 | Hefti | ..................... | A61F 2/2412 623/1.26 |
| 2010/0297218 A1 * | 11/2010 | Gong | ................... | A61L 24/043 424/450 |
| 2017/0056166 A1 * | 3/2017 | Ratz | ...................... | A61F 2/2418 |
| 2017/0112619 A1 * | 4/2017 | Curley | ................. | A61F 2/2418 |
| 2017/0196686 A1 * | 7/2017 | Tien | ..................... | A61L 27/3625 |
| 2017/0209265 A1 * | 7/2017 | Karapetian | ........... | A61F 2/2418 |

FOREIGN PATENT DOCUMENTS

| | | |
|---|---|---|
| WO | 2010049160 A1 | 5/2010 |
| WO | WO2011/109450 | 9/2011 |
| WO | 2014145811 A1 | 9/2014 |

OTHER PUBLICATIONS

PCT/US2017/012354, PCT Partial International Search, dated Apr. 19, 2017, 8pages.

* cited by examiner

BIOPROSTHETIC TISSUE REPAIR AND REINFORCEMENT

BACKGROUND

Various types and configurations of prosthetic heart valves are used to replace diseased natural human heart valves. The actual shape and configuration of any particularly prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprosthesis or mechanical heart valves prosthesis.

The bioprostheses or "tissue valves" are generally made of a suitable animal tissue or materials (e.g., harvested porcine valve leaflets, bovine or equine pericardial leaflets, synthetic material leaflets, etc.) that may be mounted onto a stationary metal or plastic frame, referred to as a "stent". Regardless of whether a stent is provided, bioprosthetic/synthetic heart valves are generally tubular (i.e., when the leaflets are "open", an internal passage is defined through which fluid (e.g., blood) can flow), and include a sewing or suture ring.

Leaflets made of biological material can have naturally occurring defects including fenestrations or split on the cut edge of the leaflets. A leaflet including the defect will typically be discarded during production of the valve or the prosthetic heart valve including the defect will be discarded at some other time prior to use in a patient. Additionally, the biological material of the leaflets is penetrated with sutures to assemble the leaflets into the prosthetic heart valve. This can cause weakened points in the biological material.

In order to increase the amount of useable leaflets for prosthetic heart valves, repair of fenestrations, splits, and other defects in the leaflets is desired. Additionally, reinforcement of select areas of the valve, including along suture lines, is desirable.

SUMMARY

One aspect provides a method of reinforcing or repairing a bioprosthetic tissue for use as a prosthetic valve leaflet. The method includes evaluating a bioprosthetic tissue, identifying a defect in the bioprosthetic tissue, and selectively applying an adhesive to a surface of the bioprosthetic tissue at the defect prior to implantation in a patient.

Another aspect provides a method of constructing a prosthetic heart valve. The method includes fixating a bioprosthetic tissue, cutting the bioprosthetic tissue to form valve leaflets, assembling a prosthetic heart valve including suturing the valve leaflets to a valve frame, and selectively applying an additive compound to the valve leaflets at suturing holes.

Another aspect provides a valve assembly including a valve frame, and prosthetic valve leaflets formed of bioprosthetic tissue assembled to the valve frame with mounting members, at least one of the prosthetic valve leaflets including an adhesive applied at a select area including a defect on a surface of the leaflet.

DETAILED DESCRIPTION

Biologic tissue used in bioprosthetic valves can have select areas that are desirable to strengthen without changing the properties, such as flexibility, of the overall tissue. For example, tissue can include naturally occurring defects such as openings or fenestrations which do not affect the performance or function of the valve. The fenestration is a cosmetic defect and native porcine aortic root tissue is often discarded due to these naturally occurring fenestrations in the leaflets. Additionally, defects such as suture openings can be imparted on the tissue during the fabrication process in assembling the valve. Reinforcing or strengthening at the specific areas of these defects is desirable prior to valve implantation in a patient, in particular, during the valve fabrication process. Additionally, focally altering biologic tissue to increase strength or stiffness may be desirable in other select areas of the tissue may be desirable. Tissue reinforcing can increase the available tissue, and heart valves produced from the tissue, that is deemed acceptable for patient implantation.

Figure 1:
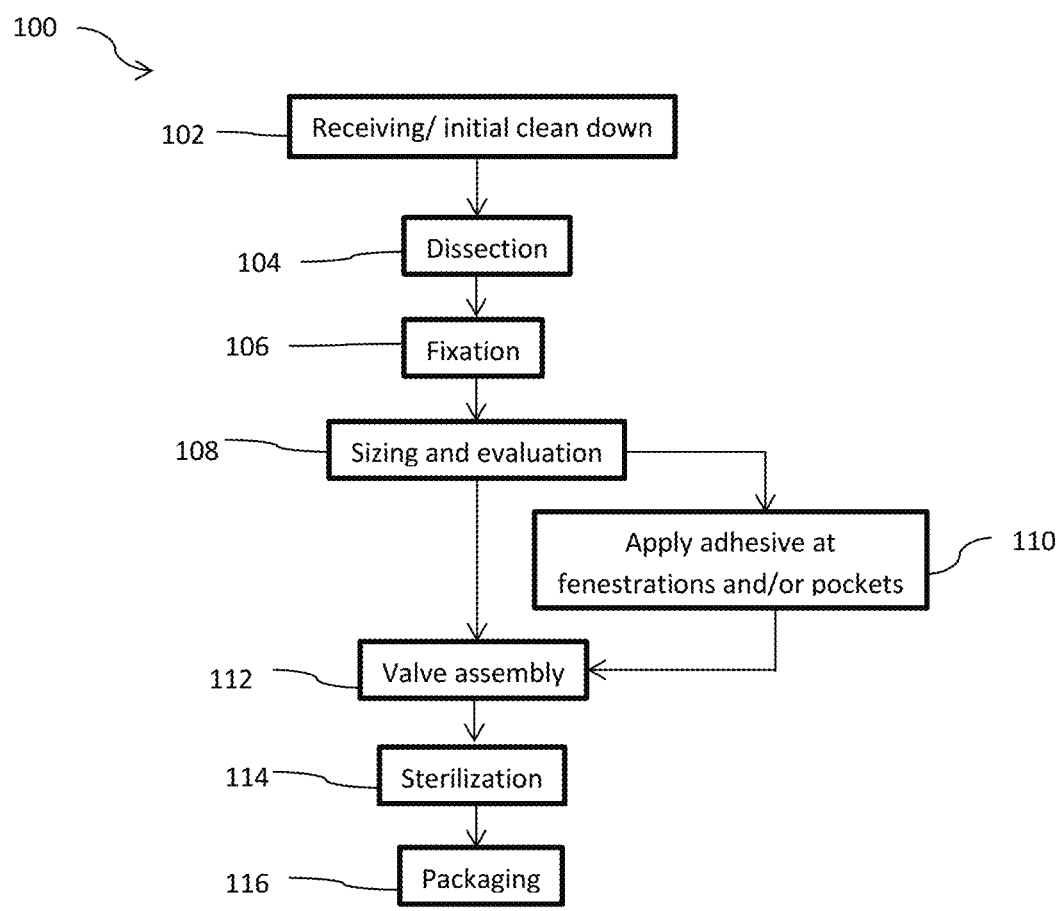
FIG. 1 is a flow diagram of an exemplary method of tissue reinforcement in accordance with aspects of the present disclosure.

FIG. 1 illustrates a flow diagram of a method 100 of fabricating a heart valve including an aortic root tissue reinforcement. A number of steps are involved in the process of preparing bioprosthetic tissue for heart valve leaflets. An initial step 102 includes receiving and initial cleaning the aortic root tissue of muscle tissue. Step 102 occurs as soon as possible after harvesting the tissue from a biological source. After the initial cleaning the tissue, the tissue is dissected and further cleaned of adherent fat or loose connective tissue in step 104. After the step 104 of dissection, the tissue is placed in a solution for the step 106 of fixation of the entire tissue. Fixation of the tissue causes cross-linking of the collagen and the protein-like compounds associated with the collagen and is performed to preserve the ultra-structure of the connective tissue. Fixation can be accomplished using a glutaraldehyde of other suitable fixative. The tissue can then be sized and evaluated for defects at step 108 for use in a prosthetic valve. A fenestration or other defect may be observed in any of the steps 102-108, particularly in step 108. An observed fenestration or pocket defect in the tissue is identified for repair.

In accordance with aspects of this disclosure, tissue with fenestrations or other defects are repaired during or after sizing and evaluation at step 110 and continue through the valve fabrication process. An adhesive, or additive compound, can be selectively applied to the observed fenestration or defect. The adhesive can be biologically derived (with collagen) or a synthetic polymer that provides added strength to the pericardial tissue in local areas. For example, the adhesive can be formed using a chemical, such as glutaraldehyde, and a protein. Alternatively, the adhesive can be a cyanoacrylate adhesive, for example. Other adhesives that are biocompatible and bind to tissue may also be acceptable. Regardless, the adhesive is selectively applied to an exterior surface of the tissue in the specific area of the fenestration or other defect to provide additional strength or closure of the fenestration or other defect. The adhesive is applied only in the specific areas of the tissue, and can change physical properties at the specific areas of adhesive application, without changing the properties, such as flexibility, of the overall tissue.

In one embodiment, a small volume of a glutaraldehyde/protein adhesive is preloaded in a dual cartridge syringe for application at the site of the fenestration. The protein and glutaraldehyde of the adhesive are held in separate containers or cartridges and not mixed until the adhesive is dispensed. As the adhesive is dispensed, the protein and glutaraldehyde mix in a predetermined ratio of protein to glutaraldehyde, starting the adhesive curing process. The adhesive may be directly applied to the tissue surface in a controlled manner or applied to the tissue using a separate applicator. An applicator, in some cases, can provide for increased precision of applying the adhesive to the tissue surface in the desired area. In one embodiment, the adhesive is used to fill a volume defined by a perimeter of the fenestration in the tissue at step 110. In some embodiments, the fenestration is 0.1 mm to 1.0 mm in diameter and the fenestration is covered/filled across the diameter and the adhesive is allowed to dry thus.

At step 112, the tissue leaflets are assembled together to form the prosthetic heart valve. The leaflets can be assembled together along with a suture ring or support structure to form the prosthetic heart valve. The leaflets are assembled using sutures or other suitable mounting members. After assembly, the valve is sterilized at step 114 and then packaged at step 116 in preparation for delivery to a surgical facility and implantation in a patient.

Figure 2:
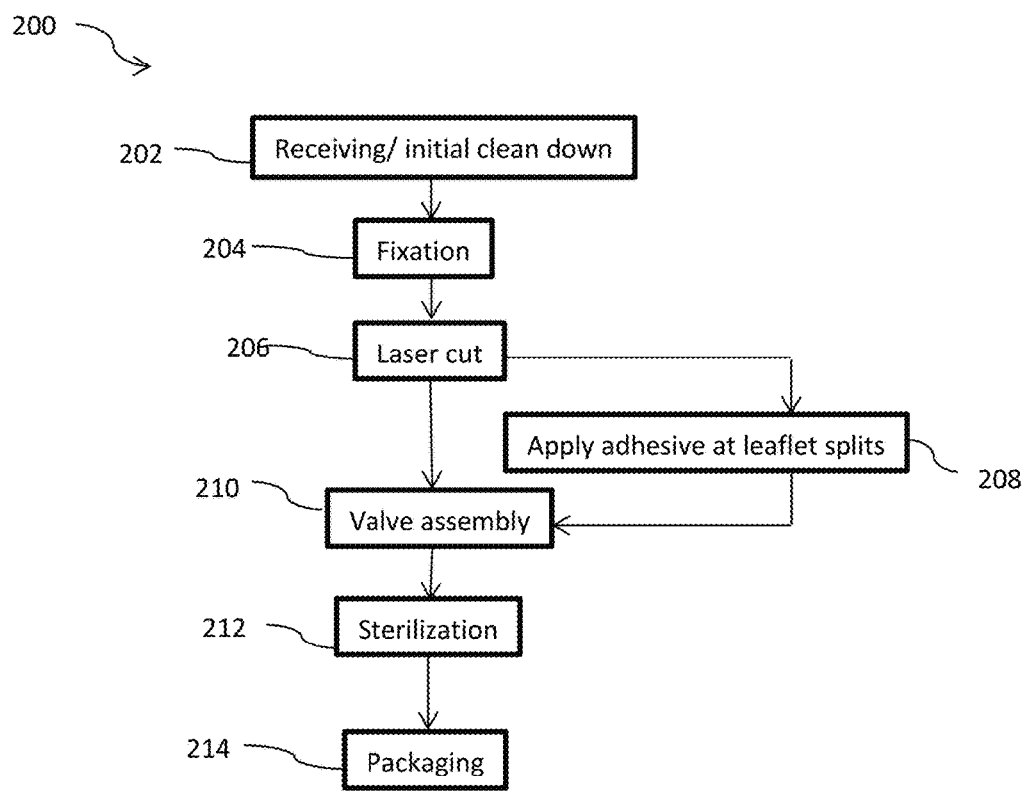
FIG. 2 is a flow diagram of an exemplary method of tissue reinforcement in accordance with aspects of the present disclosure.

FIG. 2 illustrates a flow diagram of a method 200 of fabricating a valve including repairing, or reinforcing, a pericardium leaflet. Pericardial leaflets are often discarded as unacceptable for use in a heart valve due to splits, or separation, of tissue layers. Tissue splits are typically 3 mm to 4 mm in length. Typically during inspection, if a split is observed the tissue is discarded as unusable. In accordance with the method 200 of tissue repair, tissue that would otherwise be discarded during bio-sorting due to splits is held for repair and assembly into a valve.

Method 200 includes step 202 of receiving and cleaning the pericardial leaflet of adherent fat or loose connective tissue. Step 202 occurs as soon as possible after harvesting the pericardial tissue from the biological source. After cleaning the tissue, the tissue is placed in a solution for the step 204 of fixation of the entire tissue. Fixation can be accomplished using a glutaraldehyde or other suitable fixative. At step 206, the pericardium leaflet is cut (e.g., laser cut or die cut) to the proper size and shape for use in a prosthetic valve. Areas of the leaflet tissue that are split may be observed in any of the steps 202-206, particularly in step 206. Adhesive is applied to the observed split in the tissue at step 208. A small volume of adhesive such as a glutaraldehyde/protein adhesive or a cyanoacrylate adhesive, for example, is applied to the split to seal the tissue layers together. In one embodiment, as discussed above with respect to the method embodied in FIG. 1, the protein and glutaraldehyde are held in separate containers and not mixed until the adhesive is dispensed. As the adhesive is dispensed the protein and glutaraldehyde mix in a predetermined ratio of protein to glutaraldehyde starting the curing process. Alternatively, the adhesive can be a cyanoacrylate adhesive and mixing during dispensing is not necessary. Upon curing of the adhesive, the split in the tissue at the area of adhesive application is sealed. At step 210, the valve is assembled. At step 212, the assembled valve is sterilized, and then at step 214, the assembled valve is packaged.

Figure 3:
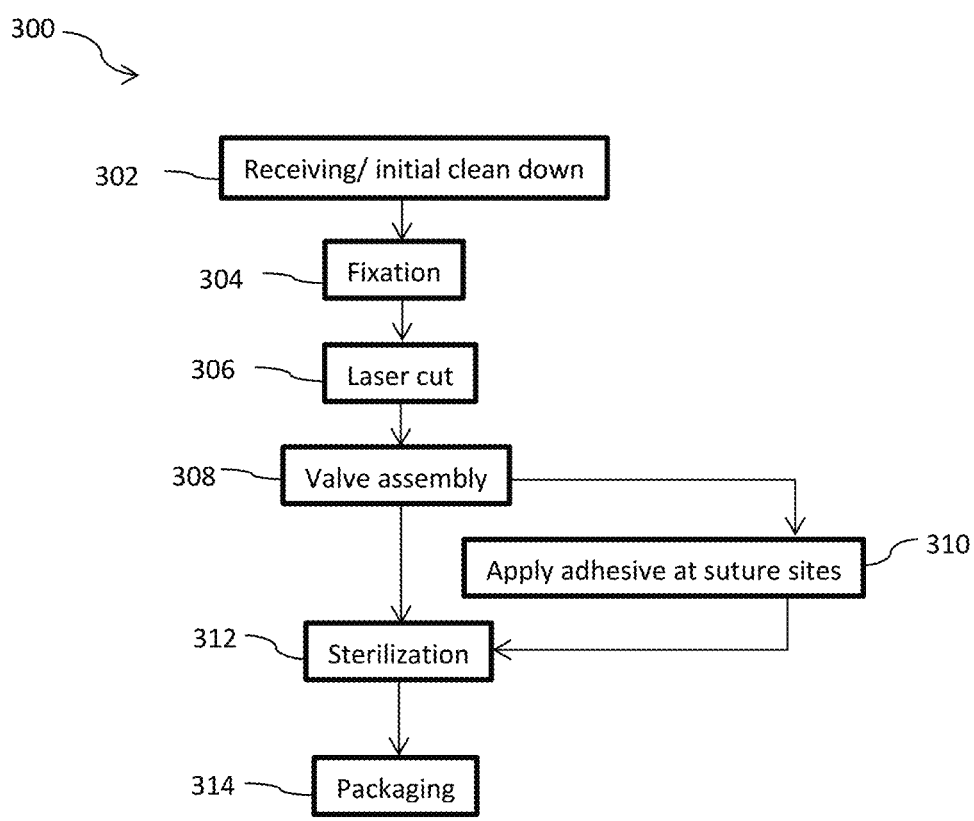
FIG. 3 is a flow diagram of an exemplary method of tissue reinforcement in accordance with aspects of the present disclosure.

FIG. 3 illustrates a flow diagram of a method 300 of fabricating a heart valve including locally reinforcing a tissue. The tissue can be pericardium tissue, for example. At step 302, the tissue is received and cleaned from adherent fat or loose connective tissue as soon as possible after harvesting. After step 302, the tissue is placed in a solution for the step 304 of fixation of the entire tissue. Step 304 of fixation can be accomplished using a glutaraldehyde or other suitable fixative. At step 306, the tissue is cut into leaflets of the appropriate size(s) and shapes(s) for assembly into the desired prosthetic valve. In one embodiment, step 306 is accomplished with a laser cutter. At step 308, the leaflets are assembled together along with a suture ring and/or support structure to form the prosthetic heart valve. The leaflets can be assembled using suturing or other suitable mounting members.

Suturing during assembly can impart damage to the tissue by putting a suture hole in the tissue. Suture holes are typically 0.1 mm to 0.5 mm in size. At step 310, an adhesive is applied locally at the suturing sites, or holes, to reinforce the tissue at the suturing sites. Specifically, a thin layer of the adhesive reinforcement material with high radial resistance can be added on the leaflet at the suturing site, such as a suture line. The adhesive, or additive compound, can be biologically derived (with collagen) or a synthetic polymer that provides added strength to the pericardial tissue in local areas. In one embodiment, the adhesive is applied at the suturing sites in a thickness of less than 100 µm. Other thickness may also be suitable. The added adhesive reinforcement material occupies a small, localized leaflet surface area and allows the pericardium leaflet tissue to withstand much higher suture pull force than otherwise available. As with the previous embodiments, the valve assembly is sterilized (step 312) and then packaged (step 314) for use at a surgical facility.

Figure 4A:
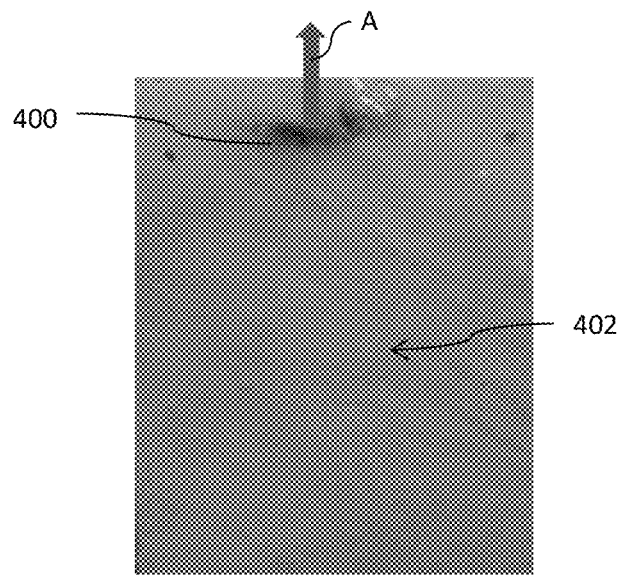
FIG. 4A is an illustration of a suture site of a tissue.
Figure 4B:
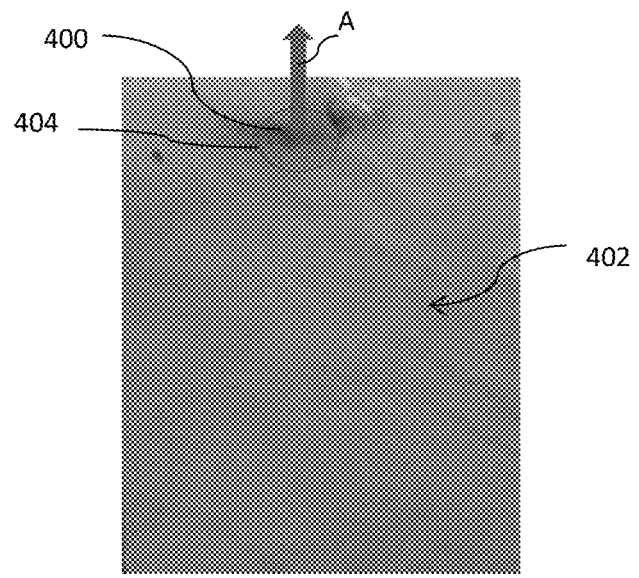
FIG. 4B is an illustration of a suture site of a tissue with a localized reinforced area in accordance with aspects of the present disclosure.

FIG. 4A illustrates a suture site 400 of a bioprosthetic tissue 402. The suture site 400 in FIG. 4A is untreated. A pull out direction is indicated by arrow "A" of a suture (not shown) at the suture site 400. FIG. 4B is an illustration of the suture site 400 of the bioprosthetic tissue 402 with a localized reinforced area 404 in accordance with aspects of the present disclosure. The tissue 402 in FIG. 4B includes an adhesive selectively applied to form the localized reinforced area 404. A pull out direction is again indicated by arrow "A" of a suture (not shown) at the suture site 400 illustrated in FIG. 4B. The tissue 402 at, or immediately surrounding, the suture site 400 having a localized reinforced adhesive treatment area 404 schematically illustrated in FIG. 4B obtains a greater tensile strength and a higher load value at failure than the untreated tissue at the suture site illustrated in FIG. 4A. In one example, the tissue at the untreated suture site has an ultimate tensile stress of 1.1 MPa (mega pascal) and the tissue at the suture site having the adhesive treatment area has an ultimate tensile stress of greater than 1.6 MPa. In one example, the untreated suture site tissue obtains a load at failure of approximately 3 N (newton) and the tissue at the localized reinforced adhesive treatment area obtains a load at failure of approximately 6 N.

Figure 5:
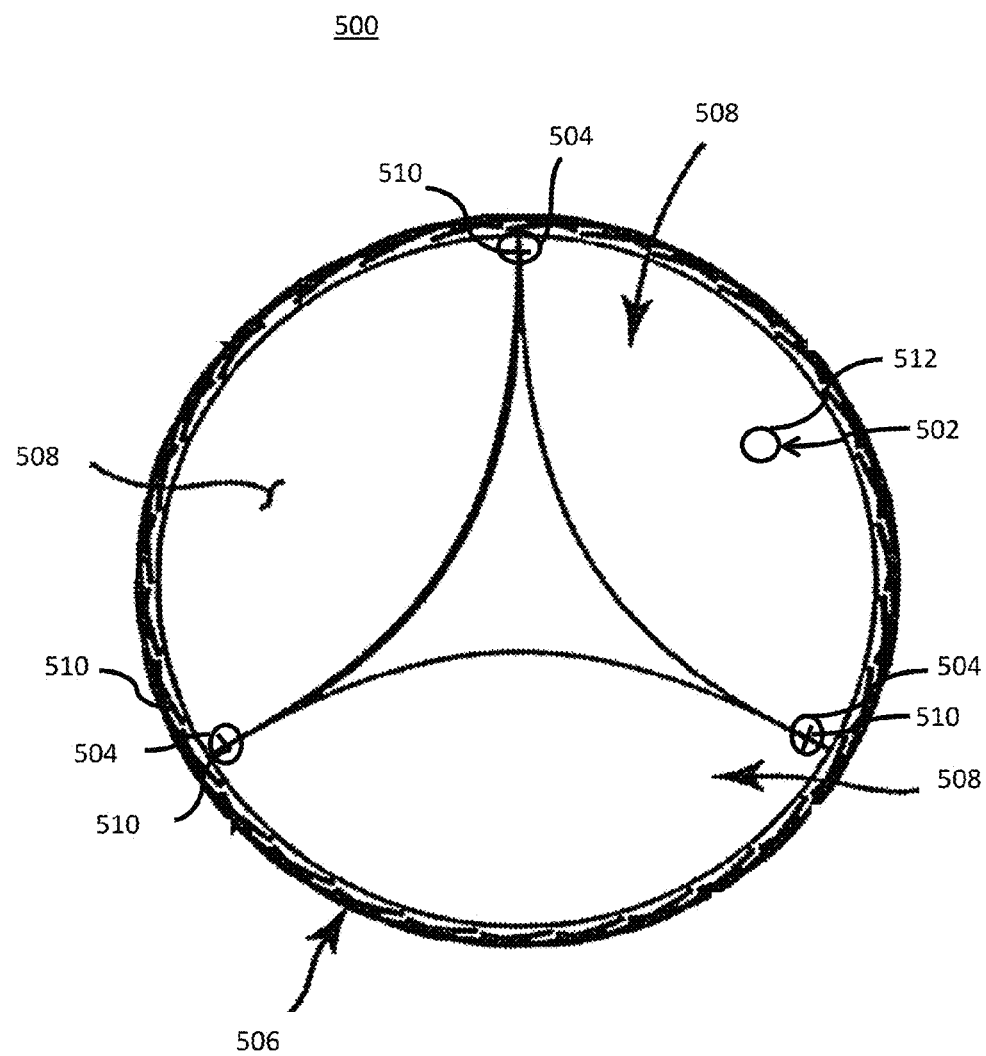
FIG. 5 is an end view of an exemplary prosthetic heart valve including localized treatment areas in accordance with aspects of the present disclosure.

FIG. 5 illustrates an exemplary prosthetic heart valve 500 including localized treatment areas 502, 504 in accordance with aspects of the present disclosure. The prosthetic heart valve 500 of FIG. 5 includes a support structure 506 and prosthetic valve leaflets 508 formed of bioprosthetic tissue assembled to the valve frame 506 with mounting members 510, such as sutures. At least one of the prosthetic valve leaflets 508 includes adhesive selectively applied at localized reinforcement areas 502 at an area of desired reinforcement 512, such as a fenestration or other defect, for example, at a surface of the leaflet 508 as described above with respect to the methods of FIGS. 1 and 2. The leaflets 508 can also include local adhesive reinforcement areas 504 of adhesive selectively applied to the prosthetic valve leaflet 508 at penetration openings formed by the sutures 510 or other suitable mounting members as described in the method of FIG. 3. The localized treatment areas 502, 504 can be any local area on the leaflets that is desirable to focally or locally alter the mechanical properties of the tissue (e.g., increasing the mechanical stiffness and strength) with the selective application of the adhesive, or additive compound.

In one embodiment, the adhesive is applied in a thickness of less than 100 µm although other thicknesses of locally applied adhesive may also be suitable. The adhesive locally alters the bioprosthetic tissues by locally modifying tissue properties, such as stiffness and strength, for example. The adhesive, or additive compound, cured on the tissue surface and can be detected with a surface chemical analysis using an X-Ray Tightness Scanner (XTS), for example. Other methods or devices of detecting the adhesive can also be used as suitable. The adhesive can be applied directly from a syringe onto the tissue and then distributed at the local tissue area as desired or the adhesive can be distributed to an applicator for application to the local tissue area. Notably, the methods of treating bioprosthetic tissue described above can be employed in a variety of bioprosthetic tissue applications and is not limited to tissue used in a prosthetic heart valve in accordance with this disclosure.

Although the present disclosure has been described with reference to preferred embodiments, workers skilled in the art will recognize that changes can be made in form and detail without departing from the spirit and scope of the present disclosure.

What is claimed is:

1. A method of reinforcing a bioprosthetic tissue for use as a prosthetic valve leaflet, comprising:
   evaluating a bioprosthetic tissue, the bioprosthetic tissue comprised of harvested naturally occurring tissue or synthetic material;
   identifying at least one defect in the bioprosthetic tissue; and
   selectively applying an adhesive to a surface of the bioprosthetic tissue at the at least one defect to locally reinforce or repair the bioprosthetic tissue prior to assembling the tissue into a prosthetic valve.

2. The method of claim 1, wherein the step of selectively applying includes preparing the adhesive by mixing a protein and glutaraldehyde as the adhesive is selectively applied.

3. The method of claim 2, wherein the protein and the glutaraldehyde are separately contained until the adhesive is selectively applied.

4. The method of claim 2, wherein the glutaraldehyde and the protein are mixed in a predetermined ratio.

5. The method of claim 2, wherein the protein is albumin.

6. The method of claim 1, wherein the adhesive is cyanoacrylate.

7. The method of claim 1, wherein the step of selectively applying the adhesive includes filling a fenestration with the adhesive such that the adhesive extends across the fenestration to contact tissue at a perimeter of the fenestration.

8. The method of claim 1, wherein the defect is a separation of tissue layers and the step of selectively applying seals the layers together.

9. The method of claim 1, further comprising after the step of selectively applying the adhesive:
   assembling the tissue into a prosthetic valve, including suturing the bioprosthetic valve leaflets to a valve frame; and
   selectively applying the adhesive to the leaflets at suturing sites.

10. The method of claim 1, wherein the adhesive includes collagen.

11. The method of claim 1, wherein the adhesive is synthetic.

12. A valve assembly, comprising:
   a valve frame; and
   prosthetic valve leaflets formed of bioprosthetic tissue assembled to the valve frame with mounting members, the bioprosthetic tissue comprised of harvested naturally occurring tissue or synthetic material, at least one of the prosthetic valve leaflets including a defect and including an adhesive applied at a select area including the defect to locally reinforce or repair the bioprosthetic tissue at the defect, wherein the defect comprises a fenestration or a separation of tissue layers, and wherein the defect is reinforced or repair prior to the prosthetic valve leaflets being assembled to the valve frame.

13. The valve assembly of claim 12, further comprising the adhesive applied to the prosthetic valve leaflet at a select area of penetration openings formed by the mounting members.

14. The valve assembly of claim 13, wherein the adhesive is less than 100 µm thick at the penetration openings.

15. The valve assembly of claim 12, wherein the select area has a greater tensile strength than an untreated area of the leaflet.

16. The valve assembly of claim 12, wherein the adhesive is comprised of protein and glutaraldehyde.

17. The valve assembly of claim 16, wherein the protein is albumin.

18. The valve assembly of claim 12, wherein the adhesive is cyanoacrylate.

* * * * *